United States Patent
Kogoi et al.

(10) Patent No.: US 8,298,507 B2
(45) Date of Patent: Oct. 30, 2012

(54) FINE PARTICULATE TITANIUM DIOXIDE, AND PRODUCTION PROCESS AND USE THEREOF

(75) Inventors: Hisao Kogoi, Toyama (JP); Susumu Kayama, Toyama (JP); Jun Tanaka, Tokyo (JP)

(73) Assignee: Showa Denko K.K., Tokyo (JP)

( * ) Notice: Subject to any disclaimer, the term of this patent is extended or adjusted under 35 U.S.C. 154(b) by 69 days.

(21) Appl. No.: 12/939,090

(22) Filed: Nov. 3, 2010

(65) Prior Publication Data

US 2011/0044888 A1 Feb. 24, 2011

Related U.S. Application Data

(62) Division of application No. 11/660,057, filed as application No. PCT/JP2005/015039 on Aug. 11, 2005, now abandoned.

(60) Provisional application No. 60/602,649, filed on Aug. 19, 2004.

(30) Foreign Application Priority Data

Aug. 11, 2004 (JP) .................................. 2004-234764

(51) Int. Cl.
*C01G 23/047* (2006.01)

(52) U.S. Cl. ........................................ 423/613; 423/610

(58) Field of Classification Search ........... 423/610–616
See application file for complete search history.

(56) References Cited

U.S. PATENT DOCUMENTS

| 2,488,439 | A | 11/1949 | Schaumann |
| 3,253,889 | A | 5/1966 | Wildt et al. |
| 4,083,946 | A | 4/1978 | Schurr et al. |
| 6,075,203 | A * | 6/2000 | Wang et al. ................... 136/256 |
| 6,444,189 | B1 * | 9/2002 | Wang et al. ................... 423/610 |
| 6,720,202 | B2 * | 4/2004 | Wang ................................ 438/85 |
| 7,591,991 | B2 * | 9/2009 | Kayama et al. ............... 423/610 |
| 2002/0106321 | A1 | 8/2002 | Tanaka et al. |
| 2002/0182310 | A1 * | 12/2002 | Wang ......................... 427/126.1 |

FOREIGN PATENT DOCUMENTS

| EP | 1 231 186 A1 | 8/2002 |
| EP | 1 243 555 A1 | 9/2002 |
| JP | 08-089785 A | 4/1996 |
| JP | 10-251021 A | 9/1998 |
| JP | 2003-064281 A | 3/2003 |
| SU | 635 044 T | 11/1978 |
| WO | WO 01/16027 A1 | 3/2001 |
| WO | WO 01/23305 A1 | 4/2001 |
| WO | 03/074426 | 9/2003 |

OTHER PUBLICATIONS

Stremilova et al., "Dechlorination of titanium dioxide", CA Database accession No. 90:124022; XP002356083 abstracting SU 635 044, published: Nov. 30, 1978.

* cited by examiner

*Primary Examiner* — Colleen Dunn
*Assistant Examiner* — Anthony J Zimmer
(74) *Attorney, Agent, or Firm* — Sughrue Mion, PLLC

(57) ABSTRACT

A process for producing a fine particulate titanium dioxide, comprising charging a fine particulate titanium dioxide powder in a resin bag, spraying water droplets having a liquid droplet diameter of 5 to 500 μm to the powder in the bag, and closing the bag for storing the powder in the bag.

9 Claims, 1 Drawing Sheet

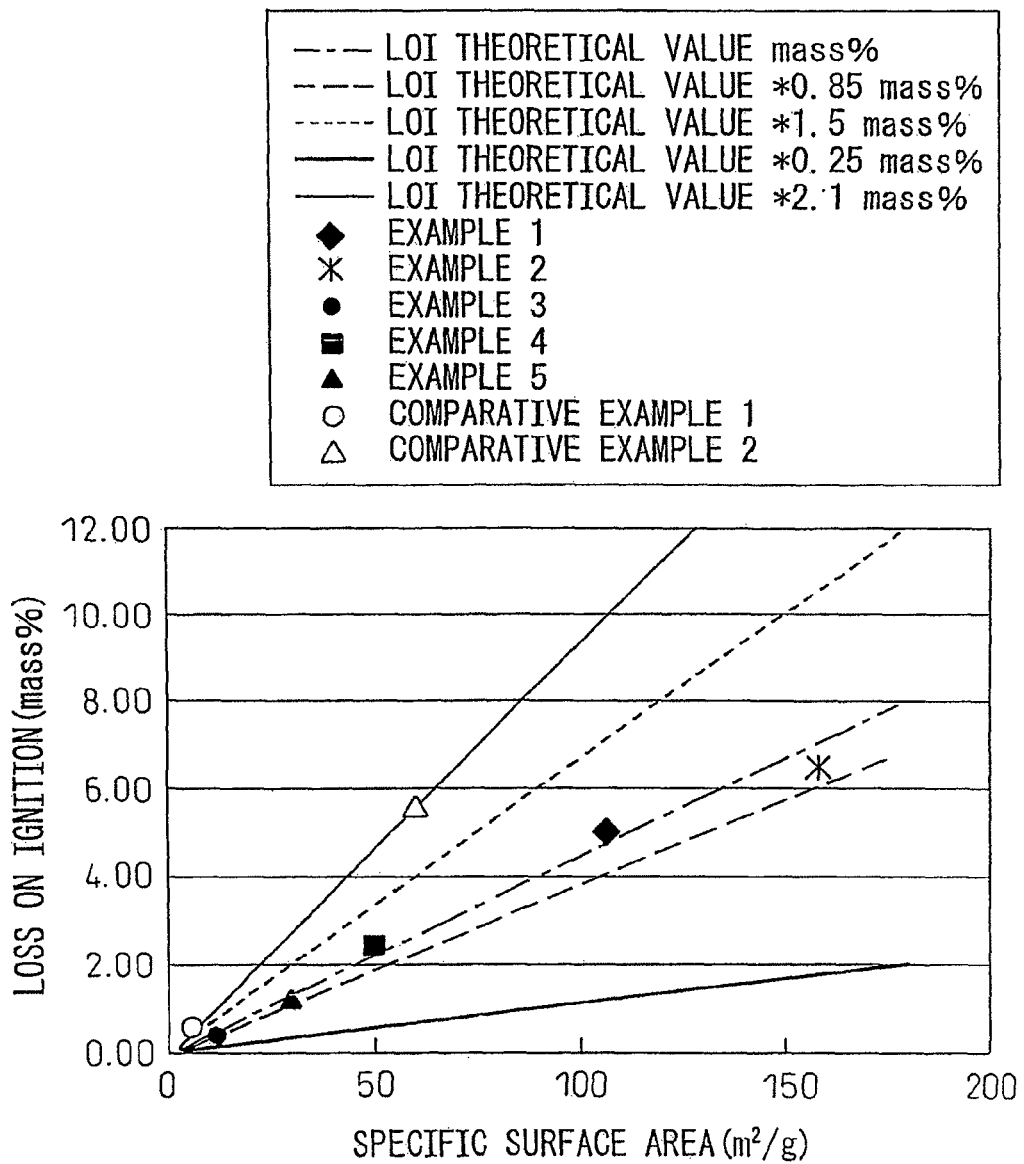

FINE PARTICULATE TITANIUM DIOXIDE, AND PRODUCTION PROCESS AND USE THEREOF

CROSS REFERENCE TO RELATED APPLICATION

This application is a Divisional of U.S. application Ser. No. 11/660,057 filed on Feb. 19, 2008, which is a National Stage of International Application No. PCT/JP2005/015039 filed Aug. 11, 2005, and which claims benefit of U.S. Provisional Application No. 60/499,367 filed on Aug. 19, 2004, the contents of which are incorporated herein by reference.

TECHNICAL FIELD

The present invention relates to a fine particulate titanium dioxide ($TiO_2$) and a production process thereof. More specifically, the present invention relates to a fine particulate titanium dioxide, obtained by a vapor phase process starting from titanium tetrachloride, which ensures a small rate of change of mass and is suitable for photocatalysts, solar cells, additives and dielectric raw materials, and also relates to a production process and uses thereof.

BACKGROUND ART

A fine particulate titanium dioxide has been heretofore used in various applications such as a UV-shielding material, an additive to silicone rubber, a dielectric raw material and a cosmetic material. In recent years, application to photocatalysts, solar cells and the like is attracting much attention.

As for the crystal form of titanium dioxide, three types of rutile, anatase and brookite, are present and among these, anatase or brookite titanium dioxide more excellent in the photoelectrochemical activity than the rutile is used in the fields of photocatalyst and solar cell.

The photocatalytic activity of titanium dioxide is utilized, for the decomposition of organic materials, as antimicrobial tiles, self-cleaning building materials and deodorant fibers, and the mechanism thereof is understood to be as follows. The titanium dioxide absorbs ultraviolet light and generates an electron and a hole in the inside thereof. The hole reacts with the adsorbed water of titanium dioxide to produce a hydroxy radical and, by the effect of this radical, the organic material adsorbed to the surface of the titanium dioxide particles is decomposed into carbonic acid gas or water (Akira Fujishima, Kazuhito Hashimoto and Toshiya Watanabe, *Hikari Clean Kakumei* (*Light Clean Revolution*), CMS (1997)).

That is, the conditions required of the titanium dioxide having strong photocatalytic activity are to readily generate a hole and to allow the hole to easily reach the titanium dioxide surface. Examples of the titanium dioxide having high photocatalytic activity include those of anatase type, those having a small number of crystal defects, and those of giving a small particle having a large specific surface area (Kazuhito Hashimoto and Akira Fujishima (compilers), *Sannka Titan Hikari Shokubai no Subete* (*All About Titanium Oxide Photocatalyst*), CMC (1998)).

In practice, titanium dioxide is fixed to the surface of a substrate with a binder and when light is irradiated onto that layer, a catalytic activity is realized. Transparency of a photocatalytic layer is demanded for the aesthetic reasons. Accordingly, when titanium dioxide is supported on a substrate, the amount of titanium dioxide and dispersibility of the powder are very important.

As for the application to solar cells, a dye-sensitized solar cell comprising a combination of a titanium dioxide and a ruthenium-base dye was reported in 1991 by Graetzel et al. of EPFL-Lausanne and, since this discovery, studies are being made thereon (M. Graezel, *Nature*, 353, 737 (1991)).

In the dye-sensitized solar cell, the titanium dioxide plays the role of a support for the dye as well as of an n-type semiconductor and is used as a dye electrode bound to an electrically conducting glass electrode. The dye-sensitized solar cell has a structure where an electrolytic layer is sandwiched by a dye electrode and a counter electrode, where the dye absorbs light and thereby generates an electron and a hole. The electron generated is transferred to the electrically conducting glass electrode through the titanium dioxide layer and taken outside. On the other hand, the generated hole is transferred to the counter electrode through the electrolytic layer and combines with an electron supplied through the electrically conducting glass electrode. One of the factors for improving the characteristic feature of a dye-sensitized solar cell is that the titanium dioxide and the dye are easily combined. As for the crystal form of titanium dioxide which can be easily combined with the dye, for example, JP-A-10-255863 (the term "JP-A" as used herein means an "Japanese Unexamined Patent Publication (Kokai)") describes use of an anatase type, and JP-A-2000-340269 states that a brookite type is suitable for dye-sensitized solar cells.

To bring out the function of titanium dioxide, good dispersibility is important. For example, when the titanium dioxide is used as a photocatalyst, if the dispersibility is bad, the covering property is intensified and the usable application is restricted. A titanium dioxide having bad dispersibility hardly transmits light and, therefore, also in the field of solar cells, the amount of titanium dioxide capable of contributing to the light absorption is limited and the photoelectric conversion efficiency decreases. In general, it is considered that light scattering (covering power) becomes maximum when the particle diameter is about a half of the visible light wavelength, and as the particle size becomes smaller, the light scattering is weakened (Manabu Kiyono, *Sannka-Titan* (*Titanium Oxide*), p. 129, Gihodo-Shuppan (1991)).

The primary particle diameter of the titanium dioxide used in the above-described field is from several nm to tens of nm in many cases and, therefore, as long as the dispersibility is good, the effect on the light scattering is small. If the titanium dioxide has poor dispersibility and gives an aggregated particle having a large diameter, light scattering is intensified. Therefore, the particle having good dispersibility can be said to be a particle which is free from aggregation and can be stably present in a state close to a primary particle in a solvent.

The titanium dioxide is an indispensable material as a high-performance dielectric raw material. The dielectric material, for example, $BaTiO_3$ is obtained by the following reaction under heating:

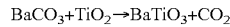

$$BaCO_3 + TiO_2 \rightarrow BaTiO_3 + CO_2$$

In order to enhance the dielectric property of $BaTiO_3$, the $BaTiO_3$ particle must be pulverized. The reaction above is a solid phase reaction and it is said that $BaCO_3$ is first decomposed at a high temperature to produce $BaO$, and the $BaO$ is diffused and solid-dissolved in the $TiO_2$ particle and becomes $BaTiO_3$. Accordingly, the size of the $BaTiO_3$ particle is governed by the size of the $TiO_2$ particle. The chlorine contained in the $TiO_2$ particle is present by adsorbing on an extreme surface layer of the particle and reacts with $BaO$ produced during heating to produce $BaCl_2$. This $BaCl_2$ is melted and acts as a flux to bring about aggregation of $TiO_2$ particles or $BaTiO_3$ particles. Also, the melted flux is readily localized and many aggregations occur in the localized portion, as a result, the quality differs from other portions. In addition, when the particles are aggregated, the $BaTiO_3$ particle crystal grows into an abnormal particle and thus decreases the dielectric property of $BaTiO_3$. during the synthesis of a high-performance dielectric material, the ratio of BaO and $TiO_2$ must be strictly controlled to be 1:1, but the presence of chlorine causes deviation from the compositional ratio.

Furthermore, fluctuation of the adsorbed water on the particle surface gives rise to a problem greater than the above-described impurity. In use of a titanium dioxide, it is required in many cases to very strictly control the blended Ti content. Particularly, in the case of using the titanium dioxide as the dielectric raw material, the blended components must be controlled even to the ppm order. However, in industrial use, strict control of raw materials is not easy, because the water is a substance present in the atmosphere where the raw materials are handled, and great difficulties are involved in the control of the amount of chemically adsorbed water and physically adsorbed water on the particle surface.

The titanium oxide surface is fundamentally covered with an OH group chemically bonded to a Ti atom or an O atom, and a water molecule is physically adsorbed to this OH group in many layers by hydrogen bonding and forms a water content measured as the loss on drying (Manabu Kiyono, *Sannka Titan* (*Titanium Oxide*), p. 54, Gihodo Shuppan (1991)).

However, this water content is readily affected by the season or weather because moisture is repeatedly absorbed or released according to the ambient humidity. Therefore, in order to strictly control the ratio of BaO and $TiO_2$, the materials must be bone-dry and weighed immediately before the synthesis and this imposes an large load in view of equipment and expense. Furthermore, as the particle is finer, the surface area per unit mass, namely, the specific surface area is larger and therefore, the amount of water adsorbed and the quantitative fluctuation of the raw material charged are larger. Combined with recent tendency toward fine particle formulation, the fluctuation of the charged amount and in turn, the reduction of the yield cannot be avoided.

The production process of titanium dioxide is roughly classified into a liquid phase process of hydrolyzing titanium tetrachloride or titanyl sulfate, and a vapor phase process of reacting titanium tetrachloride with an oxidative gas such as oxygen or water vapor. According to the liquid phase process, a titanium dioxide comprising anatase as the main phase can be obtained but this is in a sol or slurry state. In the case of using the titanium dioxide in this state, the application is limited. For using the titanium dioxide as a powder, the sol or slurry must be dried, but when dried, intensive aggregation generally results (Shinnroku Saito (superviser), Cho-Biryushi Handbook (Handbook of Ultrafine Particles), p. 388, Fuji-Technosystem Corporation, (1990)).

In the case of using this titanium dioxide as a photocatalyst or the like, the titanium oxide must be strongly cracked or ground so as to elevate the dispersibility, but this may cause problems such as mingling of abraded materials attributable to the grinding treatment or the like, and a non-uniform particle size distribution.

On the other hand, the titanium dioxide by a vapor phase process is excellent in the dispersibility as compared with that obtained by a liquid phase process, because a solvent is not used (Shinnroku Saito (superviser), Cho-Biryushi Handbook (Handbook of Ultrafine Particles), p. 388, Fuji-Technosystem Corporation, (1990)).

A large number of methods are known for obtaining ultrafine particulate titanium dioxide by a vapor phase process. For example, a process of producing a titanium dioxide by hydrolyzing titanium tetrachloride in flame is disclosed, wherein the reaction is performed by adjusting the molar ratio of oxygen, titanium tetrachloride and hydrogen to obtain a titanium dioxide having a high rutile content (JP-A-03-252315). Also, a process of producing a crystalline titanium dioxide powder by hydrolyzing titanium tetrachloride in a high-temperature vapor phase and rapidly cooling the reaction produce is disclosed, wherein the flame temperature and the titanium concentration in the raw material gas are specified to obtain a crystalline transparent titanium dioxide having an average primary particle diameter of 40 to 150 nm (JP-A-7-316536).

As for the process of producing a titanium dioxide comprising anatase as the main phase by a vapor phase process, for example, a production process where the rutile content ratio is adjusted by changing the ratio of hydrogen in an oxygen/hydrogen mixed gas in the vapor phase reaction is disclosed and a titanium dioxide having a rutile content of 9% is described, but the particle diameter of the titanium dioxide described is from 0.5 to 0.6 μm and coarser than the particle diameter range of particles generally called an ultrafine particle (JP-A-3-252315).

In the case of using a titanium dioxide for a photocatalyst or a solar cell, the fluctuation of loss on drying of titanium dioxide causes change in the formulation and this gives rise to fluctuation of quality and reduction of performance and yield.

Also, impurities such as Fe, Al, Si and S in the titanium dioxide give rise to a fluctuation in quality and reductions of performance and yield and therefor, their content is preferably reduced. For example, when Fe is present in titanium dioxide, coloration is caused and the titanium dioxide is not suited for usage where transparency is required. Also, when a component such as Al and S is present inside the titanium dioxide particle, crystal defects are generated and the function as a photocatalyst or a solar cell may be deteriorated.

As for the production process of titanium dioxide, when a titanium dioxide is produced by a vapor phase process starting from titanium tetrachloride, an ultrafine particle may be readily obtained, but chlorine originated in the raw material often remains in the titanium dioxide and dechlorination by heating, water washing or the like is required. The method for this treatment such as heating or water washing greatly affects the amount of water or hydroxyl group chemically adsorbing to the titanium dioxide particle surface. Such surface properties of titanium dioxide, including the residual chlorine, have a great effect not only on the amount of adsorbed water but also on the sintering or aggregation behavior of particles with each other at the heating in use of the titanium dioxide. Particularly, as the titanium dioxide particle is finer, the ratio of atoms present on the surface increases and the effect of the surface state becomes greater.

The present invention has been made to solve the above-described problems and an object of the present invention is to provide a fine particulate titanium dioxide with reduced fluctuation of the adsorbed water content which is a great mass fluctuation factor in a fine particulate powder body, more preferably a high-purity ultrafine particulate titanium dioxide and a production process thereof.

DISCLOSURE OF THE INVENTION

As a result of intensive investigations to solve those problems, the present inventors have found that when the conditions for the synthesis and high-purity formulation in the vapor phase process are adjusted, the amount of the hydroxyl group present on the titanium dioxide surface can be made sufficiently large and in turn, an ultrafine particulate titanium dioxide hardly undergoing fluctuation of mass in any environment can be produced. The above-described object can be attained based on this finding.

That is, in a preferred embodiment of the present invention, a fine particulate titanium dioxide stabilized in the loss on ignition and mass fluctuation in a normal environment, and an ultrafine particulate titanium dioxide having specific features in view of the particle size distribution and the coarse particle are provided, which are obtained by a vapor phase process of reacting a titanium tetrachloride-containing gas with an oxidative gas (water vapor or a mixed gas containing oxygen and water vapor), wherein the raw material gases are reacted while controlling the heating temperature of these gases and the kind and amount of the oxidative gas and, then, the heating temperature and the amount of water vapor added at the dechlorination treatment by heating are controlled. Also, a production process thereof is provided.

The present invention includes the following matters.

[1] A fine particulate titanium dioxide having a BET specific surface area of 10 to 200 m²/g, wherein when a powder of the titanium dioxide in an amount of 2 to 5 g is spread in a 10 cm-diameter glass-made Petri dish to a uniform thickness and left standing in an environment at 20° C. and a relative humidity of. 80% for 5 hours, the rate of change of mass based on the mass before standing is from −5 mass % to 5 mass %.

[2] The fine particulate titanium dioxide as described in [1] above, wherein the 90% cumulative mass-particle size distribution diameter (hereinafter denoted as "D90") is 2.2 μm or less.

[3] The fine particulate titanium dioxide as described in [1] or [2] above, wherein the distribution constant n according to the Rosin-Rammler formula represented by the following formula (1) is from 1.7 to 3.5:

$$R = 100 \exp(-bD^n) \tag{1}$$

wherein D is a particle diameter, R is a mass percentage of particles larger than D (particle diameter) based on the mass of all particles, and n is a distribution constant.

[4] A fine particulate titanium dioxide wherein, assuming that the BET specific surface area is a (m²/g) and the mass decrement when the powder is ignited in an electric furnace kept at 900° C. for 1 hour (hereinafter this decrement is called a loss on ignition) is X (mass %), the loss on ignition X is present in the range represented by formula (2):

$$2.1 \times \{\alpha/(6 \times 10^4) \times 18 + (\alpha-\beta)/(6 \times 10^4) \times 9\} \times 100 \geq X \geq 0.25 \times \{\alpha/(6 \times 10^4) \times 18 + (\alpha-\beta)/(6 \times 10^4) \times 9\} \times 100 \tag{2}$$

wherein β is a BET specific surface area (m²/g) after the powder is ignited in an electric furnace kept at 900° C. for 1 hour.

[5] A fine particulate titanium dioxide, wherein assuming that the BET specific surface area is a (m²/g) and the mass decrement when the powder is ignited in an electric furnace kept at 900° C. for 1 hour (hereinafter this decrement is called a loss on ignition) is X (mass %), the loss on ignition X is present in the range represented by formula (2'):

$$1.3 \times \{\alpha/(6 \times 10^4) \times 18 + (\alpha-\beta)/(6 \times 10^4) \times 9\} \times 100 \geq X \geq 0.7 \times \{\alpha/(6 \times 10^4) \times 18 + (\alpha-\beta)/(6 \times 10^4) \times 9\} \times 100 \tag{2'}$$

wherein β is a BET specific surface area (m²/g) after the powder is ignited in an electric furnace kept at 900° C. for 1 hour.

[6] A fine particulate titanium dioxide, wherein assuming that the BET specific surface area is a (m²/g) and the mass decrement when the powder is ignited in an electric furnace kept at 900° C. for 1 hour (hereinafter this decrement is called a loss on ignition) is X (mass %), the loss on ignition X is present in the range represented by formula (3):

$$1.5 \times \{\alpha/(6 \times 10^4) \times 18 + (\alpha-\beta)/(6 \times 10^4) \times 9\} \times 100 \geq X \geq 0.85 \times \{\alpha/(6 \times 10^4) \times 18 + (\alpha-\beta)/(6 \times 10^4) \times 9\} \times 100 \tag{3}$$

wherein β is a BET specific surface area (m²/g) after the powder is ignited in an electric furnace kept at 900° C. for 1 hour.

[7] A fine particulate titanium dioxide, wherein assuming that the BET specific surface area is α (m²/g) and the mass decrement when the powder is ignited in an electric furnace kept at 900° C. for 1 hour (hereinafter this decrement is called a loss on ignition) is X (mass %), the loss on ignition X is present in the range represented by formula (3'):

$$1.15 \times \{\alpha/(6 \times 10^4) \times 18 + (\alpha-\beta)/(6 \times 10^4) \times 9\} \times 100 \geq X \geq 0.85 \times \{\alpha/(6 \times 10^4) \times 18 + (\alpha-\beta)/(6 \times 10^4) \times 9\} \times 100 \tag{3'}$$

wherein β is a BET specific surface area (m²/g) after the powder is ignited in an electric furnace kept at 900° C. for 1 hour.

[8] The fine particulate titanium dioxide as described in any one of [1] to [7] above, wherein the Fe, Al and S contents each is 10 ppm by mass or less.

[9] The fine particulate titanium dioxide as described in any one of [1] to [8] above, wherein the content of Cl in the powder body is 50 mass % or less of the loss on ignition.

[10] A process for producing a fine particulate titanium dioxide, comprising a first step of high-temperature oxidizing a titanium tetrachloride-containing gas with use of an oxidative gas to produce a titanium dioxide powder, and a second step of contacting water vapor with the titanium dioxide powder while rolling the powder in a heating furnace, thereby effecting dechlorination and at the same time, increasing the adsorbed water.

[11] The process for producing a fine particulate titanium dioxide as described in [10] above, wherein the oxidative gas is water vapor.

[12] The process for producing a fine particulate titanium dioxide as described in [11] above, wherein the amount of water vapor contacted is from 2 to 30 mol per mol of the titanium tetrachloride gas.

[13] The process for producing a fine particulate titanium dioxide as described in any one of [10] to [12] above, wherein the titanium tetrachloride-containing gas and the oxidative gas supplied to the reaction tube each is preheated at a temperature of 600° C. to less than 1,100° C.

[14] The process for producing a fine particulate titanium dioxide as described in any one of [10] to [13] above, wherein in the second step, the water vapor and the powder body are counter-currently contacted by introducing the water vapor into the heating furnace to occupy a ratio of 1 to 50 mass % based on the titanium dioxide powder.

[15] The process for producing a fine particulate titanium dioxide as described in any one of [10] to [14] above, wherein in the second step, the water vapor and the powder body are counter-currently contacted by introducing the water vapor into the heating furnace to occupy a ratio of 1 to 50 mass % based on the titanium dioxide powder.

[16] The process for producing a fine particulate titanium dioxide as described in any one of [10] to [15] above, wherein in the second step, the titanium dioxide is heated at 150 to 500° C.

[17] The process for producing a fine particulate titanium dioxide as described in any one of [10] to [16] above, wherein in the second step, the residence time of the powder in the heating furnace is from 0.5 hours to less than 3 hours.

[18] A process for producing a fine particulate titanium dioxide, comprising spraying water droplets having a liquid droplet diameter of 5 to 500 μm at the time of packing the powder in a resin bag, and closing and then storing the bag.

[19] A fine particulate titanium dioxide produced by the process described in any one of [10] to [18] above.

[20] A perovskite compound using the fine particulate titanium dioxide described in any one of [1] to [9] and [19] above as a part of the raw materials.

[21] A dielectric raw material comprising the titanium dioxide powder described in any one of [1] to [9] and [19] above.

[22] A slurry comprising the titanium dioxide powder described in any one of [1] to [9] and [19] above.

[23] A composition comprising the titanium dioxide powder described in any one of [1] to [9] and [19] above.

[24] A photocatalyst material comprising the titanium dioxide powder described in any one of [1] to [9] and [19] above.

[25] A cosmetic material comprising the titanium dioxide powder described in any one of [1] to [9] and [19] above.

[26] A solar cell material comprising the titanium dioxide powder described in any one of [1] to [9] and [19] above.

[27] An additive for silicone rubber, comprising the titanium dioxide powder described in any one of [1] to [9] and [19] above.

According to a preferred production process of the present invention, a fine particulate titanium dioxide reduced in the change of mass and an ultrafine particulate titanium dioxide having specific features in view of the particle size distribution and the coarse particle are obtained.

As a result, in the industrial use of titanium dioxide, a titanium dioxide which can dispense with a step of strictly measuring the Ti content in advance by the measurement of loss on ignition or the like can be obtained, so that not only the production cost can be reduced but also the amount of the titanium dioxide blended can be controlled with good precision.

The thus-produced fine particulate titanium dioxide is, despite its large specific surface area, reduced in the quantitative fluctuation of the raw material charged, so that in uses as a pigment of various compositions, a UV-shielding material, an additive to silicone rubber, clothes, a dielectric raw material or a raw material of a cosmetic material, a photocatalyst, a solar cell or the like, a remarkable effect of less causing fluctuation of quality, reduction of performance and decrease of yield is exerted.

BRIEF DESCRIPTION OF THE DRAWING

FIG. 1 is a graph showing the BET specific surface area and the loss on ignition of fine particulate titanium oxide produced in Examples and Comparative Examples.

BEST MODE FOR CARRYING OUT THE INVENTION

The present invention is described in detail below.

Usually, when using a titanium dioxide in an industrial scale, the charged amount of the raw material component is strictly controlled and, for this purpose, the loss on ignition, loss on drying and the like are measured and based on the measured values, the charged amount is correctly modified. However, the adsorption/release of moisture rapidly proceeds and the amount of water adsorbed in the time period from analysis to measurement of the charged amount gives rise to an error in the amount charged. Therefore, even when the charged amount is correctly modified, it is very difficult to strictly control the charged amount of the Ti content.

An ultrafine particulate titanium dioxide (the titanium dioxide as used in the present invention includes all of those which are simply referred to as "titanium oxide") as a preferred embodiment of the present invention is reduced in the change of mass. In a normal titanium dioxide, an OH group is chemically bonded to a Ti atom on the surface, and a water molecule is bonded to the OH group in many layers by hydrogen bonding to form physically adsorbed water layers. The bonding of this physically adsorbed water is considered to be weaker as the layer is remoter from the titanium dioxide surface, that is, on the outer side. Therefore, as the number of constituted layers is larger, the mass is more susceptible to the environment and more fluctuates. In the titanium dioxide as a preferred embodiment of the present invention, the stratum allowing for adsorption of water is considered to be low in layer number and the fluctuation of the mass is small.

More specifically, the titanium dioxide as a preferred embodiment of the present invention is characterized in that when the powder in an amount of 2 to 5 g is spread in a 10 cm-diameter glass-made Petri dish to a uniform thickness and left standing in an environment at 20° C. and a relative humidity of 80% for 5 hours, the rate of change of mass based on the mass before standing is from −5 mass % to 5 mass %, preferably from −4.5 mass % to 4.5 mass %, more preferably from −4 mass % to 4 mass %, further preferably from −2.5 mass % to 2.5 mass %.

In this fine particulate titanium dioxide powder, the specific surface area of the powder body as measured by the BET method is from 10 to 200 m$^2$/g, preferably from 20 to 180 m$^2$/g, and at the same time, the 90% cumulative mass-particle size distribution diameter D90 is preferably 2.2 μm or less. This means that coarse particles are less present and the powder is suitable for usage where a fine particle is required. Also, in the particle size distribution, the distribution constant n according to the Rosin-Rammler formula represented by the following formula (1) is preferably from 1.7 to 3.5. The distribution constant n shows the degree of uniformity of the particle size and as the numerical value of n is larger, the particle size uniformity is judged to be more excellent.

$$R = 100\exp(-bD^n) \quad (1)$$

In formula (1), D is a particle diameter, R is a mass percentage of particles larger than D based on the mass of all particles, n is a distribution constant, and b is a factor showing the particle size property. The Rosin-Rammler formula is described in *Ceramic Kogaku Handbook* (*Ceramic Engineering Handbook*), compiled by Nippon Ceramics Kyokai, 1st ed., pp. 596-598, Gihodo-Shuppan (1989).

Furthermore, a fine particulate titanium dioxide powder, in which assuming that the specific surface area of the powder body as measured by the BET method is a (m$^2$/g) and the mass decrement when the powder is ignited in an electric furnace kept at 900° C. for 1 hour (hereinafter this decrement is called a loss on ignition) is X (mass %), the loss on ignition X is preferably present in the range represented by formula (2):

$$2.1 \times \{\alpha/(6 \times 10^4) \times 18 + (\alpha-\beta)/(6 \times 10^4) \times 9\} \times 100 \geq X \geq 0.25 \times \{\alpha/(6 \times 10^4) \times 18 + (\alpha-\beta)/(6 \times 10^4) \times 9\} \times 100 \quad (2)$$

more preferably by formula (2'):

$$1.3 \times \{\alpha/(6 \times 10^4) \times 18 + (\alpha-\beta)/(6 \times 10^4) \times 9\} \times 100 \geq X \geq 0.7 \times \{\alpha/(6 \times 10^4) \times 18 + (\alpha-\beta)/(6 \times 10^4) \times 9\} \times 100 \quad (2'),$$

or preferably, in the range represented by formula (3):

$$1.5 \times \{\alpha/(6 \times 10^4) \times 18 + (\alpha-\beta)/(6 \times 10^4) \times 9\} \times 100 \geq X \geq 0.85 \times \{\alpha/(6 \times 10^4) \times 18 + (\alpha-\beta)/(6 \times 10^4) \times 9\} \times 100 \quad (3),$$

more preferably by formula (3'):

$$1.15 \times \{\alpha/(6 \times 10^4) \times 18 + (\alpha - \beta)/(6 \times 10^4) \times 9\} \times 100 \geq X \geq 0.85 \times \{\alpha/(6 \times 10^4) \times 18 + (\alpha - \beta)/(6 \times 10^4) \times 9\} \times 100 \quad (3')$$

is reduced in the rate of change of mass as compared with conventional titanium dioxide powders and is suitable for a raw material required to assure a precise charged amount. In formulae (2), (2'), (3) and (3'), β is a specific surface area (m²/g) of powder body measured by the BET method after the powder is ignited in an electric furnace kept at 900° C. for 1 hour.

Meanings of formulae (2), (2'), (3) and (3') are described below. These two formulae are based on the following formula (4), where α and β have the same meanings as in formula (2), (2'), (3) or (3').

$$\{\alpha \times 10 \times 10^{18}/(6 \times 10^{23}) \times 18 + \{(\alpha - \beta) \times 10 \times 10^{18}\}/(6 \times 10^{23}) \times 0.5 \times 18 \quad (4)$$

This formula is divided into the following two formulae:

$$\{\alpha[m^2/g] \times 10 \times 10^{18} [\text{pieces/m}^2]\}/(6 \times 10^{23}) [\text{pieces/mol}] \times 18 [\text{g/mol}] \quad (5)$$

$$\{(\alpha - \beta) [m^2/g] \times 10 \times 10^{18} [\text{pieces/m}^2]\}/(6 \times 10^{23}) [\text{pieces/mol}] \times 0.5 \times 18 [\text{g/mol}] \quad (6)$$

It is said that on the surface of titanium dioxide particle, about $10 \times 10^{18}$ [pieces/m²] of OH is present in the case of rutile and about $13 \times 10^{18}$ [pieces/m²] of OH is present in the case of anatase [Manabu Kiyono, *Sannka Titan* (*Titanium Oxide*), p. 54, Gihodo-Shuppan (1991))]. Each of this number of OH groups on the rutile particle surface is bonded to one $H_2O$ molecule and, considering that these are eliminated as water due to heating at the measurement of loss on ignition, the mass ratio of water eliminated from the particle is represented by formula (5).

At the measurement of loss on ignition, the heating is performed at 900° C. When heated, the titanium dioxide undergoes particle growth and is decreased in the specific surface area. This decrement is represented by $(\alpha - \beta)$ [m²/g]. That is, a route allowing for elimination of the OH group due to decrease in the specific surface area during heating may also be considered. At this time, one molecular of water is produced from two molecules of OH group on the titanium dioxide surface and therefore, in formula (6), 0.5 is multiplied. Accordingly, the mass ratio of water which is eliminated resulting from decrease in the surface area is represented by formula (6).

The eliminated water measured as a loss on ignition is the sum of formulae (5) and (6), that is, formula (4). Then, a certain range is imparted to formula (4) and this is formula (2), (2'), (3) or (3').

In the fine particulate titanium dioxide as a preferred embodiment of the present invention, the contents of Fe, Al and S each is preferably 10 ppm by mass or less. The titanium dioxide obtained by the vapor phase process uses a high-purity titanium tetrachloride as the raw material and therefore, mingling of impurities can be suppressed. The concentration of such an impurity is preferably lower but in view of the apparatus material, raw material purity and the like, higher purity incurs higher cost. In the industrial use, the lower limit of each substance is actually about 2 ppm by mass.

The titanium dioxide as a preferred embodiment of the present invention is characterized by high dispersibility. This is considered to result because the reaction at the particle production is performed in an atmosphere rich in water vapor and therefore, the particle surface is fully covered with a water molecule or an OH group. In the present invention, a particle size distribution is measured as an index of dispersibility by employing a laser diffraction-type particle size distribution measuring method. According to Shinroku Saito (supervisor), *Cho-Biryushi Handbook* (*Handbook of Ultrafine Particles*), page 93, Fujitechnosystem Corporation (1990), the measuring method for dispersibility includes a precipitation method, a microscope method, a light scattering method, a direct counting method and the like and out of these, the precipitation method and the direct counting method are not suitable for the measurement of dispersibility of ultrafine particles, because the measurable particle diameter is hundreds of nm or more. In the microscope method, the measured value may fluctuate according to sampling of the objective sample or pretreatment of the sample, and this method is also not preferred. On the other hand, the light-scattering method can measure a particle diameter in the range from several nm to several μm and is suitable for the measurement of ultrafine particles. The dispersibility is preferably measured by a particle size distribution measurement method using a laser diffraction particle size distribution measuring apparatus. For example, Microtrac HRA (Nikkiso Co. Ltd.) or ALD-2000J (Shimadzu Corporation) can be used for the measurement. The procedure for measuring the particle size distribution is described below.

A slurry obtained by adding 50 ml of pure water and 100 μl of an aqueous 10% sodium hexametaphosphate solution to 0.05 g of titanium dioxide is irradiated with an ultrasonic wave (46 KHz, 65 W) for 3 minutes. Then, this slurry is measured of the particle size distribution by a laser diffraction-type particle size measuring apparatus (SALD-2000J, manufactured by Shimadzu Corporation). As the D90 value in the thus-measured particle size distribution is smaller, the dispersibility in a hydrophilic solvent is judged higher. The 50% cumulative mass-particle size distribution diameter may also be used as an index of dispersibility, but it is difficult to detect an aggregated particle of which dispersibility is bad.

In the ultrafine particle titanium dioxide of the present invention, D90 is preferably 2.2 μm or less.

The production process is described below.

A general production process of titanium dioxide by a vapor phase process is known, where titanium tetrachloride is oxidized by using an oxidative gas such as oxygen or water vapor under the reaction condition of about 1,000° C. to obtain a fine particulate titanium dioxide.

In a preferred embodiment of the present invention, a vapor phase process of high-temperature oxidizing a titanium tetrachloride-containing gas with an oxidative gas to produce a titanium dioxide is employed. Preferably, a titanium tetrachloride-containing gas heated to 600° C. to less than 1,100° C. and an oxidative gas (preferably water vapor) heated to 600° C. to less than 1,100° C. are supplied to a reaction tube. More preferably, the titanium dioxide obtained by the reaction is allowed to reside in the reaction tube under the temperature condition of 800° C. to less than 1,100° C. and then dechlorinated while counter-currently contacting an oxidative gas with the powder body under the condition of 150 to 500° C., whereby an ultrafine particulate titanium dioxide reduced in the change of mass, and in which water is satisfactorily and stably bound to the titanium dioxide surface, is obtained.

The dechlorination includes a dry process and a wet process, but here a dry dechlorination method is described. For example, a method where titanium dioxide is heated by using a heating apparatus such as cylindrical rotary heating furnace, hot-air circulation heating furnace, fluidized drying furnace and stir-drying furnace, and the surface water content is stabilized while removing chlorine. However, the present invention is not limited to these heating devices. For example, a wet dechlorination method of suspending titanium dioxide in pure water and separating chlorine, having transferred to the liquid phase, out of the system may also be used. In view of stabilization of water content, a dry dechlorination method is preferred.

The temperature in a reaction tube into which the titanium tetrachloride-containing gas or water vapor is introduced is preferably from 800° C. to less than 1,100° C., more preferably from 900° C. to less than 1,000° C. By elevating the temperature in the reaction tube, the reaction is completed at the same time with mixing, so that generation of uniform nuclei can be promoted and also the reaction zone can be made small. If the temperature in the reaction tube is less than 800° C., a titanium dioxide having a high anatase content is readily obtained, but the reaction may proceed unsatisfactorily to cause chlorine to remain inside the titanium dioxide particle, whereas if the temperature in the reaction tube becomes 1,100° C. or more, transition to rutile or particle growth tends to proceed, failing in obtaining a low-rutile type ultrafine particle.

When the raw material gases are introduced and the reaction proceeds, this reaction is an exothermic reaction and therefore, there is present a reaction zone where the reaction temperature exceeds 1,100° C. Although the heat is more or less released from the apparatus, unless the titanium dioxide particle is rapidly cooled, the particle continues growing and the crystal structure may be transformed up into rutile. Therefore, in a preferred embodiment of the present invention, the high-temperature residence time at 800° C. to less than 1,100° C. is preferably set to 0.1 second or less, more preferably 0.05 seconds or less. If the high-temperature residence time exceeds 0.1 second, transition to rutile, or sintering of the particles, tends to proceed.

The means for rapid cooling is not particularly limited but for example, a method of introducing a large amount of a cooling air or a gas such as nitrogen into the reaction mixture, or a method of spraying water may be employed.

By controlling the temperature in the reaction tube to 800° C. to less than 1,100° C., an ultrafine particle having a low chlorine content inside the particle can be obtained and furthermore, by controlling the high-temperature residence time to 0.1 second or less, a transition to rutile and particle growth can be prevented.

In order to set the temperature in the reaction tube to 800° C. to less than 1,100° C., the temperature of raw material gases is preferably adjusted to 600 to 1,100° C. The heated raw material gases react in the reaction tube to generate heat, but if the raw material gas temperature is less than 600° C., the temperature in the reaction tube can be hardly elevated to 800° C. or more, whereas if the raw material gas temperature exceeds 1,100° C., the temperature in the reaction tube readily exceeds 1,100° C. despite a release of heat from the apparatus.

As for the composition of the titanium tetrachloride-containing raw material gas, the inert gas preferably occupies from 0.1 to 20 mol, more preferably from 4 to 20 mol, per mol of the titanium tetrachloride gas. If the inert gas content is less than this range, the density of titanium dioxide particles in the reaction zone increases and aggregation or sintering readily occurs, as a result, a fine particulate titanium dioxide can be hardly obtained. If the inert gas content exceeds the above-described range, the reactivity decreases and the recovery percentage as a titanium dioxide may decrease.

The amount of the water vapor reacted with the titanium tetrachloride-containing raw material gas is preferably from 2 to 30 mol, more preferably from 5 to 25 mol, per mol of titanium tetrachloride. If the ratio of the water vapor is less than this range, a water content is not satisfactorily bound to the surface of the produced titanium dioxide particle and when stored for a long time, a reaction of the titanium dioxide particle surface with the water content gradually proceeds and this gives rise to fluctuation of the mass. When the ratio exceeds the above-described range, the number of nuclei generated is increased and an ultrafine particle is readily obtained but even if it exceeds 30 mol, the effect of increasing the number of nuclei generated is scarcely obtained. Even when the amount of water vapor exceeds 30 mol, the properties of the titanium dioxide are not affected, but this upper limit is specified from the economical viewpoint. On the other hand, if the amount of the water vapor based on the titanium tetrachloride is insufficient, the titanium dioxide obtained tends to have many oxygen defects and be colored.

Dechlorination by the heating of titanium dioxide is preferably performed at a heating temperature of 150 to 500° C. while counter-currently contacting water or water vapor with the titanium dioxide powder such that the mass ratio of water and titanium dioxide (=mass of water vapor/mass of titanium dioxide, hereinafter the same) becomes from 1 to 60 mass %, preferably from 1 to 50 mass %. More preferably, the mass ratio of water and titanium dioxide is from 5 to 40 mass % and the heating temperature is from 300 to 450° C. If the heating temperature exceeds 500° C., sintering of titanium dioxide particles proceeds and particle growth is generated, whereas if the heating temperature is less than 150° C., the dechlorination efficiency seriously decreases. Chlorine on the titanium dioxide surface undergoes a displacement reaction with water in the vicinity of the particle or with a surface hydroxyl group of an adjacent particle, whereby dechlorination proceeds. Accordingly, it is very effective for the dechlorination to add water vapor while heating, and a displacement reaction between chlorine and water or OH group is preferably performed. At this time, when chlorine on the titanium dioxide particle surface is replaced with water, dechlorination is effected without causing particle growth, but when chlorine is replaced with a surface hydroxyl group of an adjacent particle, particle growth is effected simultaneously with dechlorination. That is, in order to perform the dechlorination while preventing the particle growth, it is effective to control the mass ratio of water and titanium dioxide and when the mass ratio of water and titanium dioxide is 1 mass % or more, the effect of preventing the particle growth is remarkably recognized and this is preferred.

The water vapor put into contact with the titanium dioxide may be used by mixing it with air. The air plays the role of efficiently moving the chlorine separated from titanium dioxide, out of the system. The water vapor is preferably contained in the air at a concentration of 0.1 vol % or more, more preferably 5 vol % or more, still more preferably 10 vol % or more. The water vapor-containing air is preferably heated to 200 to 1,000° C.

In the dechlorination step by heating, the residence time of powder in the rotary furnace is preferably from 0.5 hours to less than 3 hours, more preferably from 0.5 hours to less than 1 hour. This is a time period necessary for unfailingly effecting the dechlorination while preventing the particle growth. If the residence time is less than this range, insufficient dechlorination may result, whereas if it exceeds the above-described range, particle growth may proceed.

As for the production process of a titanium dioxide reduce in the rate of change of mass, a process of spraying water droplets simultaneously at the time of packing the powder in a resin bag, and closing and then storing the bag may also be used. In this process, fine water droplets are sprayed on the powder body to temporarily load water droplets on the particle and the powder body is stored in a closed packing material relatively impermeable to water content, such as a resin bag, whereby the temporarily loaded water droplets are fixed as an adsorbed water. According to this process, a water droplet can be stabilized in a very short time as an adsorbed water difficult of desorption. The liquid droplet diameter is preferably 5 to 500 µm, more preferably 5 to 300 µm. If the water droplet sprayed is large and exceeds 500 µm, the water content is locally present in the powder bodies and it takes time for the water content to become uniformly present, whereas if the water droplet diameter is less than 5 µm, the loading efficiency is bad and not practical. The water droplet in the range from 5 to 500 µm is suited for loading on titanium dioxide at 10 to 200 $m^2/g$.

Another method for producing the titanium dioxide is a method for storing a powder which has been subjected to dechlorination treatment in a high humidity environment. In this method, a powder is charged in a moisture vapor permeable package or the like and allowed to stand in a suitable temperature and high humidity environment, by which moisture can be adsorbed to a targeted content and stabilized. The suitable temperature may be an operable temperature range such as about 20-50° C. and, in winter, about 5-40° C. The high humidity means a relative humidity of 60-95%, preferably 60-90%. If the relative humidity exceeds 95%, moisture is apt to condense by room temperature change. However, in this method, a long time is required for stabilization.

A pressure reduction method, listed as one of titanium oxide dichlorination methods, can also apply. While the inside of a container is adjusted to a predetermined temperature, for example, 5-40° C., and water in an amount equal to the amount necessary to titanium oxide is supplied, a pressure reduction is then effected. As a result, chlorine is taken out from titanium oxide to outside the system and, concurrently, water molecules are adsorbed onto OH groups on the surface of titanium oxide in place of chlorine, so that the water content adsorbed on titanium oxide can increase in a relatively short time period. Here, the degree of pressure reduction is preferably 0.5 kPa or more, more preferably 0.5 kPa to 2 kPa. The degree of pressure reduction is a difference between the pressure in the container and the atmospheric pressure. The upper limit of the degree of pressure reduction is not particularly specified but economical upper limit is 2 kpa since a large scale pressure reduction apparatus is required if the pressure reduction degree increases. However, if a large amount of a powder is treated by this method, an apparatus for maintaining the reduced pressure during continuous operation and an apparatus for moving titanium oxide from a container under a reduced pressure to atmospheric pressure environment are required, which is disadvantageous from economical viewpoint.

The characteristics of water to be sprayed are not particularly limited, but removal of impurity course particles such as metal particles through a filter is preferred, and pure water in which impurities have been removed by ion exchange resin, etc. is more preferred. The temperature of water may be either normal cool water or warmed water, but warm water at 20-100° C. is preferred because it is effective in accelerating evaporation and adsorption to powder of fine water droplets.

A method for producing and spraying water droplets with a fine particle size is not particularly limited but, for example, a method for scattering water vapor using a ultrasonic humidifier or a heating steam generator, or a spraying method using a one-liquid or two-liquid spray nozzle may be used. Where a spray nozzle is used, a preferred nozzle is one which can control the average particle size of water droplets to 5-500 µm, more preferably 5-300 µm, further preferably 5-50 µm. If the diameter of water droplets exceeds 500 µm, the possibility that water unevenly distributes increases and it takes a longer time until water content distribution becomes uniform. Further, a powder easily wets and course particles due to aggregation may be formed, which is not preferred. If the diameter of water droplets is less than 5 µm, the efficiency of supporting is low and it is not practical. Water droplets having a diameter of 5-500 µm is very suitable for supporting on fine titanium oxide of 10-200 $m^2/g$. The average particle size of water droplets can be measured by laser light scattering method, phase Doppler-type laser particle analysis, or the like.

When the spray method using a two liquid-type spray nozzle is used, the properties of air used are not particularly limited, but it is preferred to remove environmental course particle impurities through a filter and air in which excess water has been removed by an air dryer or the like is more preferred. The temperature of air may be normal temperature but dry air heated to 20-100° C. is preferred because this is effective to evaporate fine water droplets and adsorb water droplets onto titanium oxide particles. An uncombustible gas such as nitrogen gas may be used in place of air. More preferably, simultaneous use of a combination of warm water heated to 20-100° C. and dry air or an uncombustible gas such as nitrogen gas heated to 20-100° C. accelerates evaporating fine water droplets and adsorbing water droplets onto titanium oxide particles, so that it is effective for water absorption and stabilization in a short time.

The thus-produced fine particulate titanium dioxide as a preferred embodiment of the present invention is a powder body having a sharp particle size distribution and being free of coarse particle and reduced in the fluctuation of mass and therefore, can be suitably used for various uses of fine particulate titanium dioxide, such as pigment of various compositions, photocatalyst, UV-shielding cosmetic material, UV-shielding clothing, material for wet solar cell, deodorant clothing, filler material for UV shielding, additive for various products (e.g., silicone rubber), and raw material of dielectric material including perovskite compound (e.g., barium titanate). The fine particulate titanium dioxide of the present invention is used as a powder body or a slurry.

Representative uses of the perovskite compound are a piezoelectric ceramic and a pyroelectric ceramic. The piezoelectric ceramic is used in a piezoelectric actuator and, for example, BT type, PZT type, PT type and BNT type are known. The pyroelectric ceramic is used in an infrared sensor or the like and, for example, PT type is known. In all of these ceramics, titanium oxide is used as a raw material. The production process of such a ceramic is not particularly limited and any known method may be employed (see, for example, "*Oyo Gijutsu*", *Biryushi Kogaku Taikei* ("*Applied Technology*", *Fine Particle Engineering Series*), Vol. 2, pp. 27-33 and 190-195). Incidentally, whichever production process is employed, it is essential to strictly control the atomic composition.

The titanium oxide is sometimes used as an abrasive slurry for hard discs and the like. In this case, the solid concentration in the abrasive slurry is an important factor governing the abrasive performance. Also, in terms of dispersion in an aqueous system, a stable dispersing operation can be achieved when the adsorbed water is stabilized. Furthermore, in use as a raw material for cosmetic materials, solar cells, photocatalysts and the like, the titanium oxide is used also as a dispersion in water, a silicon rubber-polymer, an organic polymer or the like and in view of stability in the dispersion step and blending precision determining the product composition, it is preferred that the adsorbed water present on the titanium oxide particle surface is stabilized.

EXAMPLES

The present invention is described in greater detail below by referring to Examples and Comparative Examples, but the present invention is not limited thereto.

Example 1

20 kg/hr of titanium tetrachloride diluted with 25 Nm$^3$/hr (N means that the state is reduced to a standard state of ideal gas, hereinafter the same) of nitrogen gas was preheated to 1,100° C. and introduced into a reaction tube. Similarly, 55 Nm$^3$/hr of water vapor was heated to 1,100° C. and introduced into the reaction tube and through a reaction with the titanium tetrachloride gas, fine titanium dioxide particles were obtained. These fine particles were collected in a polytetrafluoroethylene-made bag filter and then introduced into an external heating-type rotary kiln. The external heating-type rotary kiln had a structure that a stir-up blade for stirring the powder body was provided in the inside. The rotary kiln was set to a temperature of 400° C., and the residence time of the powder body was adjusted to about 1 hour by controlling the length of high-temperature zone, the rotating speed and the angle at which the kiln was installed.

Separately, water vapor in an amount of 20 mass % based on the mass of titanium dioxide passing through the kiln was introduced from the outlet for the powder body in the rotary kiln, thereby counter-currently contacting the powder body and the water vapor. Incidentally, the water vapor introduced was previously heated to approximately from 120 to 200° C.

In the thus-obtained powder body, the BET specific surface area was 107 m$^2$/g, the entire chlorine content was 8,000 ppm by mass, Fe was 2 ppm, Al was 2 ppm or less, and S was 2 ppm or less. The BET specific surface area was measured by a specific surface area meter (model: Flow Sorb II, 2300) manufactured by Shimadzu Corporation.

On the particle size distribution of the titanium dioxide powder obtained above, a 90% cumulative mass-particle size distribution diameter D90 was measured by a laser diffraction-type particle size distribution measuring method and found to be 0.9 μm.

Also, 2 g of the powder was spread in a 10 cm-diameter glass-made Petri dish to a uniform thickness and left standing in an environment at 20° C. and a relative humidity of 80% for 5 hours, and then the rate of change of mass based on the mass before standing was measured and found to be 2.3 mass %.

The mass decrement when the powder was ignited in an electric furnace kept at 900° C. for 1 hour, that is, the loss on ignition was 5.0 mass %. The BET specific surface area of the sample after the measurement of loss on ignition was 6 m$^2$/g.

Furthermore, the distribution constant n according to the Rosin-Rammler formula represented by $R=100\exp(-bD^n)$ was 2.7.

Example 2

5 kg/hr of titanium tetrachloride diluted with 25 Nm$^3$/hr of nitrogen gas was preheated to 1,100° C. and introduced into a reaction tube. Similarly, 55 Nm$^3$/hr of water vapor was heated to 1,100° C. and introduced into the reaction tube and through a reaction with the titanium tetrachloride gas, fine titanium dioxide particles were obtained. These fine particles were collected by a polytetrafluoroethylene-made bag filter and then introduced into an external heating-type rotary kiln. The external heating-type rotary kiln had a structure that a stir-up blade for stirring the powder body was provided in the inside. The rotary kiln was set to a temperature of 400° C., and the residence time of the powder body was adjusted to about 1 hour by controlling the length of high-temperature zone, the rotating speed and the angle at which the kiln was installed.

Separately, water vapor in an amount of 30 mass % based on the mass of titanium dioxide passing through the kiln was introduced from the outlet for the powder body in the rotary kiln, thereby counter-currently contacting the powder body and the water vapor. Incidentally, the water vapor introduced was previously heated to approximately from 120 to 200° C.

In the thus-obtained powder body, the BET specific surface area was 158 m$^2$/g, the entire chlorine content was 13,000 ppm by mass, Fe was 2 ppm, Al was 2 ppm or less, and S was 2 ppm or less. The BET specific surface area was measured by a specific surface area meter (model: Flow Sorb II, 2300) manufactured by Shimadzu Corporation.

On the particle size distribution of the titanium dioxide powder obtained above, a 90% cumulative mass-particle size distribution diameter D90 was measured by a laser diffraction-type particle size distribution measuring method and found to be 0.8 μm.

Also, 2 g of the powder was spread in a 10 cm-diameter glass-made Petri dish to a uniform thickness and left standing in an environment at 20° C. and a relative humidity of 80% for 5 hours, and then the rate of change of mass based on the mass before standing was measured and found to be 3.6 mass %.

The mass decrement when the powder was ignited in an electric furnace kept at 900° C. for 1 hour, that is, the loss on ignition was 6.5 mass %. The BET specific surface area of the sample after the measurement of loss on ignition was 3.5 m$^2$/g.

Furthermore, the distribution constant n according to the Rosin-Rammler formula represented by $R=100\exp(-bD^n)$ was 3.2.

Example 3

150 kg/hr of titanium tetrachloride was preheated to 900° C. and introduced into a reaction tube. Similarly, 30 Nm$^3$/hr of water vapor was heated to 900° C. and introduced into the reaction tube and through a reaction with the titanium tetrachloride gas, fine titanium dioxide particles were obtained. These fine particles were collected by a polytetrafluoroethylene-made bag filter and then introduced into an external heating-type rotary kiln. The external heating-type rotary kiln had a structure that a stir-up blade for stirring the powder body was provided in the inside. The rotary kiln was set to a temperature of 400° C., and the residence time of the powder body was adjusted to about 45 minutes by controlling the length of high-temperature zone, the rotating speed and the angle at which the kiln was installed.

Separately, water vapor in an amount of 3 mass % based on the mass of titanium dioxide passing through the kiln was introduced from the outlet for the powder body in the rotary kiln, thereby counter-currently contacting the powder body and the water vapor. Incidentally, the water vapor introduced was previously heated to approximately from 120 to 200° C.

In the thus-obtained powder body, the BET specific surface area was 12 m$^2$/g, the entire chlorine content was 1,000 ppm by mass, Fe was 2 ppm, Al was 2 ppm or less, and S was 2 ppm or less. The BET specific surface area was measured by a specific surface area meter (model: Flow Sorb II, 2300) manufactured by Shimadzu Corporation.

On the particle size distribution of the titanium dioxide powder obtained above, a 90% cumulative mass-particle size distribution diameter D90 was measured by a laser diffraction-type particle size distribution measuring method and found to be 2.2 μm.

Also, 5 g of the powder was spread in a 10 cm-diameter glass-made Petri dish to a uniform thickness and left standing in an environment at 20° C. and a relative humidity of 80% for 5 hours, and then the rate of change of mass based on the mass before standing was measured and found to be 0.12 mass %.

The mass decrement when the powder was ignited in an electric furnace kept at 900° C. for 1 hour, that is, the loss on ignition was 0.37 mass %. The BET specific surface area of the sample after the measurement of loss on ignition was 5 m$^2$/g.

Furthermore, the distribution constant n according to the Rosin-Rammler formula represented by $R=100\exp(-bd^n)$ was 1.7.

Example 4

70 kg/hr of titanium tetrachloride diluted with 20 Nm$^3$/hr of nitrogen gas was preheated to 900° C. and introduced into a reaction tube. Similarly, 50 Nm$^3$/hr of water vapor was heated to 900° C. and introduced into the reaction tube and through a reaction with the titanium tetrachloride gas, fine titanium dioxide particles were obtained. These fine particles were collected by a polytetrafluoroethylene-made bag filter and then introduced into an external heating-type rotary kiln. The external heating-type rotary kiln had a structure that a stir-up blade for stirring the powder body was provided in the inside. The rotary kiln was set to a temperature of 450° C., and the residence time of the powder body was adjusted to about 45 minutes by controlling the length of high-temperature zone, the rotating speed and the angle at which the kiln was installed.

Separately, water vapor in an amount of 10 mass % based on the mass of titanium dioxide passing through the kiln was introduced from the outlet for the powder body in the rotary kiln, thereby counter-currently contacting the powder body and the water vapor. Incidentally, the water vapor introduced was previously heated to approximately from 120 to 200° C.

In the thus-obtained powder body, the BET specific surface area was 50 m$^2$/g, the entire chlorine content was 5,000 ppm by mass, Fe was 2 ppm, Al was 2 ppm or less, and S was 2 ppm or less. The BET specific surface area was measured by a specific surface area meter (model: Flow Sorb II, 2300) manufactured by Shimadzu Corporation.

On the particle size distribution of the titanium dioxide powder obtained above, a 90% cumulative mass-particle size distribution diameter D90 was measured by a laser diffraction-type particle size distribution measuring method and found to be 1.3 μm.

Also, 5 g of the powder was spread in a 10 cm-diameter glass-made Petri dish to a uniform thickness and left standing in an environment at 20° C. and a relative humidity of 80% for 5 hours, and then the rate of change of mass based on the mass before standing was measured and found to be 1.8 mass %.

The mass decrement when the powder was ignited in an electric furnace kept at 900° C. for 1 hour, that is, the loss on ignition was 2.40 mass %. The BET specific surface area of the sample after the measurement of loss on ignition was 5.6 m$^2$/g.

Furthermore, the distribution constant n according to the Rosin-Rammler formula represented by $R=100\exp(-bD^n)$ was 1.9.

Example 5

160 kg/hr of titanium tetrachloride diluted with 23 Nm$^3$/hr of nitrogen gas was preheated to 1,050° C. and introduced into a reaction tube. Similarly, 28 Nm$^3$/hr of water vapor was heated to 1,050° C. and introduced into the reaction tube and through a reaction with the titanium tetrachloride gas, fine titanium dioxide particles were obtained. These fine particles were collected by a polytetrafluoroethylene-made bag filter and then introduced into an external heating-type rotary kiln. The external heating-type rotary kiln had a structure that a stir-up blade for stirring the powder body was provided in the inside. The rotary kiln was set to a temperature of 450° C., and the residence time of the powder body was adjusted to about 45 minutes by controlling the length of high-temperature zone, the rotating speed and the angle at which the kiln was installed.

Separately, water vapor in an amount of 4 mass % based on the mass of titanium dioxide passing through the kiln was introduced from the outlet for the powder body in the rotary kiln, thereby counter-currently contacting the powder body and the water vapor. Incidentally, the water vapor introduced was previously heated to approximately from 120 to 200° C.

In the thus-obtained powder body, the BET specific surface area was 30 m$^2$/g, the entire chlorine content was 2,500 ppm by mass, Fe was 2 ppm, Al was 2 ppm or less, and S was 2 ppm or less. The BET specific surface area was measured by a specific surface area meter (model: Flow Sorb II, 2300) manufactured by Shimadzu Corporation.

On the particle size distribution of the titanium dioxide powder obtained above, a 90% cumulative mass-particle size distribution diameter D90 was measured by a laser diffraction-type particle size distribution measuring method and found to be 0.7 μm.

Also, 5 g of the powder was spread in a 10 cm-diameter glass-made Petri dish to a uniform thickness and left standing in an environment at 20° C. and a relative humidity of 80% for 5 hours, and then the rate of change of mass based on the mass before standing was measured and found to be 1.0 mass %.

The mass decrement when the powder was ignited in an electric furnace kept at 900° C. for 1 hour, that is, the loss on ignition was 1.25 mass %. The BET specific surface area of the sample after the measurement of loss on ignition was 5.2 m$^2$/g.

Furthermore, the distribution constant n according to the Rosin-Rammler formula represented by $R=100\exp(-bD^n)$ was 3.4.

Example 6

To the titanium dioxide used in Example 4, water droplets with a liquid diameter of 30 μm were sprayed, and the titanium dioxide powder was charged and sealed in a resin bag, followed by storing the powder at a place where the temperature was set at 25±3° C. for 24 hours. 5 g of the powder was then spread in a 10 cm-diameter glass-made Petri dish to a uniform thickness and left standing in an environment at 20° C. and a relative humidity of 80% for 5 hours, and then the rate of change of mass based on the mass before standing was measured and found to be 1.4 mass %.

Example 7

To the titanium dioxide used in Example 4, water droplets with a liquid diameter of 30 μm were sprayed, and the titanium dioxide powder was charged and sealed in a resin bag, followed by storing the powder at a place where the temperature was set at 25±3° C. for 24 hours. 5 g of the powder was then spread in a 10 cm-diameter glass-made Petri dish to a uniform thickness and left standing in an environment at 20° C. and a relative humidity of 80% for 5 hours, and then the rate of change of mass based on the mass before standing was measured and found to be 0.83 mass %.

Example 8

To the titanium dioxide used in Example 5, water droplets with a liquid diameter of 30 μm were sprayed, and the titanium dioxide powder was charged and sealed in a resin bag, followed by storing the powder at a place where the temperature was set at 25±3° C. for 24 hours. 5 g of the powder was then spread in a 10 cm-diameter glass-made Petri dish to a uniform thickness and left standing in an environment at 20° C. and a relative humidity of 80% for 5 hours, and then the rate of change of mass based on the mass before standing was measured and found to be 0.74 mass %.

Comparative Example 1

180 kg/hr of titanium tetrachloride was preheated to 900° C. and introduced into a reaction tube. Similarly, 30 Nm³/hr of oxygen was heated to 900° C. and introduced into the reaction tube and through a reaction with the titanium tetrachloride gas, fine titanium dioxide particles were obtained. These fine particles were collected by a polytetrafluoroethylene-made bag filter and then introduced into an external heating-type rotary kiln. The external heating-type rotary kiln had a structure that a stir-up blade for stirring the powder body was provided in the inside. The rotary kiln was set to a temperature of 350° C., and the residence time of the powder body was adjusted to about 50 minutes by controlling the length of high-temperature zone, the rotating speed and the angle at which the kiln was installed.

In the thus-obtained powder body, the BET specific surface area was 6 m²/g, the entire chlorine content was 100 ppm by mass, Fe was 2 ppm, Al was 2 ppm or less, and S was 2 ppm or less. The BET specific surface area was measured by a specific surface area meter (model: Flow Sorb II, 2300) manufactured by Shimadzu Corporation.

On the particle size distribution of the titanium dioxide powder obtained above, a 90% cumulative mass-particle size distribution diameter D90 was measured by a laser diffraction-type particle size distribution measuring method and found to be 2.6 μm.

Also, 5 g of the powder was spread in a 10 cm-diameter glass-made Petri dish to a uniform thickness and left standing in an environment at 20° C. and a relative humidity of 80% for 5 hours, and then the rate of change of mass based on the mass before standing was measured and found to be 6 mass %.

The mass decrement when the powder was ignited in an electric furnace kept at 900° C. for 1 hour, that is, the loss on ignition was 0.6 mass %. The BET specific surface area of the sample after the measurement of loss on ignition was 5 m²/g.

Furthermore, the distribution constant n according to the Rosin-Rammler formula represented by $R=100\exp(-bD^n)$ was 1.6.

Comparative Example 2

70 kg/hr of titanium tetrachloride diluted with 25 Nm³/hr of nitrogen gas was preheated to 900° C. and introduced into a reaction tube. Similarly, 30 Nm³/hr of water vapor was heated to 550° C. and introduced into the reaction tube and through a reaction with the titanium tetrachloride gas, fine titanium dioxide particles were obtained. These fine particles were collected by a polytetrafluoroethylene-made bag filter and then introduced into an external heating-type rotary kiln. The rotary kiln was set to a temperature of 120° C., and the residence time of the powder body was adjusted to about 45 minutes by controlling the length of high-temperature zone, the rotating speed and the angle at which the kiln was installed.

In the thus-obtained powder body, the BET specific surface area was 60 m²/g, the entire chlorine content was 31,000 ppm by mass, Fe was 2 ppm, Al was 2 ppm or less, and S was 2 ppm or less.

On the particle size distribution of the titanium dioxide powder obtained above, a 90% cumulative mass-particle size distribution diameter D90 was measured by a laser diffraction-type particle size distribution measuring method and found to be 8.8 μm.

Also, 5 g of the powder was spread in a 10 cm-diameter glass-made Petri dish to a uniform thickness and left standing in an environment at 20° C. and a relative humidity of 80% for 5 hours, and then the rate of change of mass based on the mass before standing was measured and found to be 9 mass %.

The mass decrement when the powder was ignited in an electric furnace kept at 900° C. for 1 hour, that is, the loss on ignition was 5.6 mass %. The BET specific surface area of the sample after the measurement of loss on ignition was 5.1 m²/g.

Furthermore, the distribution constant n according to the Rosin-Rammler formula represented by $R=100\exp(-bD^n)$ was 1.2.

The results in Examples and Comparative Examples above are shown together in Table 1 and FIG. 1. In Table 1 and FIG. 1, "LOI theoretical value" represents a theoretical value of the loss on ignition and the straight lines of FIG. 1 show a preferred range of 0.25 to 2.1 mass % and a more preferred range of 0.85 to 1.5 mass %.

TABLE 1

| | BET, m²/g | BET after Measurement of LOI, m²/g | LOI Theoretical Value of 900° C.-1 hr, mass % | LOI Experimental Value, mass % | LOI Theoretical Value *0.85 mass % | LOI Theoretical Value *1.5 mass % | LOI Theoretical Value *0.25 mass % | LOI Theoretical Value *2.1 mass % | rate of change of mass based on mass before standing at 20° C. and 80% RH for 5 hours, mass % |
|---|---|---|---|---|---|---|---|---|---|
| Example 1 | 107 | 6 | 4.73 | 5.00 | 4.02 | 7.09 | 1.18 | 9.92 | 2.3 |
| Example 2 | 158 | 3.5 | 7.06 | 6.50 | 6.00 | 10.59 | 1.76 | 14.82 | 3.6 |
| Example 3 | 12 | 5 | 0.47 | 0.37 | 0.40 | 0.70 | 0.12 | 0.98 | 0.12 |
| Example 4 | 50 | 5.6 | 2.17 | 2.40 | 1.84 | 3.25 | 0.54 | 4.55 | 1.8 |
| Example 5 | 30 | 5.2 | 1.27 | 1.25 | 1.08 | 1.91 | 0.32 | 2.67 | 1.0 |
| Example 6 | 107 | 6.1 | 4.73 | 6.75 | 4.02 | 7.09 | 1.18 | 9.92 | 1.4 |
| Example 7 | 50 | 5.2 | 2.17 | 3.14 | 1.84 | 3.25 | 0.54 | 4.55 | 0.83 |
| Example 8 | 30 | 5 | 1.27 | 1.52 | 1.08 | 1.91 | 0.32 | 2.67 | 0.74 |
| Comparative Example 1 | 6 | 5 | 0.20 | 0.60 | 0.17 | 0.29 | 0.05 | 0.41 | 6.0 |

TABLE 1-continued

| | BET, m²/g | BET after Measurement of LOI, m²/g | LOI Theoretical Value of 900° C.-1 hr, mass % | LOI Experimental Value, mass % | LOI Theoretical Value *0.85 mass % | LOI Theoretical Value *1.5 mass % | LOI Theoretical Value *0.25 mass % | LOI Theoretical Value *2.1 mass % | rate of change of mass based on mass before standing at 20° C. and 80% RH for 5 hours, mass % |
|---|---|---|---|---|---|---|---|---|---|
| Comparative Example 2 | 60 | 5.1 | 2.62 | 5.60 | 2.23 | 3.94 | 0.66 | 5.51 | 9.0 |

LOI: Loss on ignition

INDUSTRIAL APPLICABILITY

The powder body having a narrow particle size distribution and being free from coarse particle and reduced in the fluctuation of mass is suitable for various uses. For example, this powder can be used for a pigment of various compositions, a photocatalyst, an UV-shielding cosmetic material, an UV-shielding clothing, deodorant clothing, a filler material for UV shielding, an additive for various products such as silicone rubber, a dielectric raw material, or the like.

The invention claimed is:

1. A process for producing a fine particulate titanium dioxide, comprising:
   a first step of high-temperature oxidizing a titanium tetrachloride-containing gas with use of an oxidative gas to produce a titanium dioxide powder,
   a second step of contacting water vapor with the titanium dioxide powder while rolling the powder in a heating furnace, thereby effecting dechlorination and at the same time, increasing the adsorbed water,
   a third step of packaging the powder produced in the second step in a resin bag, comprising spraying water droplets having a liquid droplet diameter of 5 to 500 μm onto the powder in the bag, and then closing the bag, and
   a fourth step of storing the powder in the bag.

2. The process for producing a fine particulate titanium dioxide according to claim 1, wherein the oxidative gas is water vapor.

3. The process for producing a fine particulate titanium dioxide according to claim 2, wherein the amount of water vapor contacted is from 2 to 30 mol per mol of the titanium tetrachloride gas.

4. The process for producing a fine particulate titanium dioxide according to claim 1, wherein the titanium tetrachloride-containing gas and the oxidative gas supplied to the reaction tube each is preheated at a temperature of 600° C. to less than 1,100° C.

5. The process for producing a fine particulate titanium dioxide according to claim 1, wherein in the second step, the water vapor and the powder are counter-currently contacted by introducing the water vapor into the heating furnace at a ratio of 1 to 60 mass % based on the titanium dioxide powder.

6. The process for producing a fine particulate titanium dioxide according to claim 1, wherein in the second step, the water vapor and the powder are counter-currently contacted by introducing the water vapor into the heating furnace at a ratio of 1 to 50 mass % based on the titanium dioxide powder.

7. The process for producing a fine particulate titanium dioxide according to claim 1, wherein in the second step, the titanium dioxide is heated at 150 to 500° C.

8. The process for producing a fine particulate titanium dioxide according to claim 1, wherein in the second step, the residence time of the powder in the heating furnace is from 0.5 hours to less than 3 hours.

9. A process for producing a fine particulate titanium dioxide, comprising charging a fine particulate titanium dioxide powder in a resin bag, spraying water droplets having a liquid droplet diameter of 5 to 500 μm onto the powder in the bag, and closing the bag for storing the powder in the bag.

* * * * *